(12) United States Patent
Montag et al.

(10) Patent No.: US 10,610,296 B2
(45) Date of Patent: Apr. 7, 2020

(54) CARDIAC ELECTROPHYSIOLOGY MACHINE INCLUDING CATHETER STABILITY WHILE ESTIMATING IMPEDANCE DROP

(71) Applicant: Biosense Webster (Israel) Ltd., Yokneam (IL)

(72) Inventors: Avram Dan Montag, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 195 days.

(21) Appl. No.: 15/610,253

(22) Filed: May 31, 2017

(65) Prior Publication Data

US 2018/0344392 A1 Dec. 6, 2018

(51) Int. Cl.

| A61B 18/12 | (2006.01) |
|---|---|
| A61B 18/14 | (2006.01) |
| A61B 5/00 | (2006.01) |
| A61B 5/053 | (2006.01) |
| A61B 18/00 | (2006.01) |

(52) U.S. Cl.
CPC ........ *A61B 18/1492* (2013.01); *A61B 5/0538* (2013.01); *A61B 5/4836* (2013.01); *A61B 2018/00351* (2013.01); *A61B 2018/00577* (2013.01); *A61B 2018/00791* (2013.01); *A61B 2018/00875* (2013.01); *A61B 2018/00982* (2013.01); *A61B 2018/00988* (2013.01)

(58) Field of Classification Search
CPC ......... A61B 5/02; A61B 5/053; A61B 5/0044; A61B 5/0245; A61B 18/14
See application file for complete search history.

(56) References Cited

U.S. PATENT DOCUMENTS

| 5,643,255 A  * | 7/1997 | Organ ................ A61B 18/1492 606/34 |
|---|---|---|
| 9,125,667 B2 * | 9/2015 | Stone ................. A61B 18/1492 |
| 2002/0077627 A1* | 6/2002 | Johnson ............ A61B 18/1477 606/41 |
| 2003/0120163 A1 | 6/2003 | Rudy et al. |
| 2003/0130711 A1 | 7/2003 | Pearson et al. |

(Continued)

OTHER PUBLICATIONS

Papez V et al, "Bio-impedance signal processing using adaptive digital filter" Telecommunication in modern satellite cable and broadcasting services (TELSIKS), 2011 10th International Conference on IEEE Oct. 5, 2011.

(Continued)

*Primary Examiner* — Daniel W Fowler

(57) ABSTRACT

A device, system and method for measuring the impedance during a medical procedure being performed on a patient is disclosed. The device, system and method include an electrode capable of being used in the medical procedure, a plurality of patches operationally located on the surface of a body of the patient, and a sensor for measuring a signal between the electrode and at least one of the plurality of patches, the signal being processed using a processor using a first filter and a second filter, and combining the result of the first filter and the second filter using a weighting of the filters to provide a measurement of the impedance, wherein the impedance indicates the end of the medical procedure.

20 Claims, 6 Drawing Sheets

(56) References Cited

U.S. PATENT DOCUMENTS

| | | | |
|---|---|---|---|
| 2005/0021104 A1* | 1/2005 | DiLorenzo | A61N 1/36082 607/45 |
| 2009/0030477 A1* | 1/2009 | Jarrard | A61B 18/1206 607/42 |
| 2010/0168557 A1* | 7/2010 | Deno | A61B 5/0422 600/424 |
| 2010/0179538 A1 | 7/2010 | Podhajsky | |
| 2011/0144524 A1 | 6/2011 | Fish et al. | |
| 2013/0165916 A1* | 6/2013 | Mathur | A61B 18/18 606/33 |
| 2013/0296679 A1* | 11/2013 | Condie | A61B 5/6856 600/374 |
| 2013/0296845 A1 | 11/2013 | Bar-Tal et al. | |
| 2014/0039490 A1 | 2/2014 | Wham | |
| 2014/0086273 A1 | 3/2014 | Gliner et al. | |
| 2015/0265347 A1* | 9/2015 | Yates | A61B 18/18 606/50 |
| 2015/0320479 A1* | 11/2015 | Cosman, Jr. | A61B 90/37 606/35 |
| 2017/0354534 A1* | 12/2017 | Paradis | A61F 7/0085 |
| 2018/0249967 A1* | 9/2018 | Lederman | A61B 5/7246 |

OTHER PUBLICATIONS

European Search Report dated Oct. 11, 2018 received in EP Patent Appln. No. 18175250.2.

* cited by examiner

CARDIAC ELECTROPHYSIOLOGY MACHINE INCLUDING CATHETER STABILITY WHILE ESTIMATING IMPEDANCE DROP

SUMMARY

A cardiac electrophysiology machine including impedance drop estimation that is based on a weighted choice between a least squares filter and a median filter is disclosed. The relative weight when combining the results from each of the two filters is based on the catheter speed. In one embodiment, the weighting is based on a logical sigmoid filter with the 50% threshold set to 1 mm/sec of catheter speed. This is a more accurate way to compensate for apparent periodic impedance changes due to respiration and heartbeat. Other weightings and filters could also be used.

The cardiac electrophysiology machine includes measuring the impedance during a medical procedure being performed on a patient. The machine includes an electrode capable of being used in the medical procedure, a plurality of patches operationally located on a body surface of the patient, and a sensor for measuring a signal between the electrode and at least one of the plurality of patches, the signal being processed using a processor applying a first filter and a second filter separately, and combining the result of the output of the first filter and the output of the second filter using a weighting to provide an output of the impedance, wherein the impedance indicates an end of the medical procedure.

The machine may include the first filter biased to provide a more accurate assessment of the impedance once the medical procedure is underway. The machine may include the first filter as a least squares filter.

The machine may include the second filter biased to provide a more accurate assessment of the impedance at the beginning of the medical procedure. The system and method may include the second filter as a median filter. The machine may include the weighting as a sigmoid filter applied to the first and second filters based on catheter speed.

BRIEF DESCRIPTION OF THE DRAWINGS

A more detailed understanding may be had from the following description, given by way of example in conjunction with the accompanying drawings wherein.

DETAILED DESCRIPTION

Figure 1:
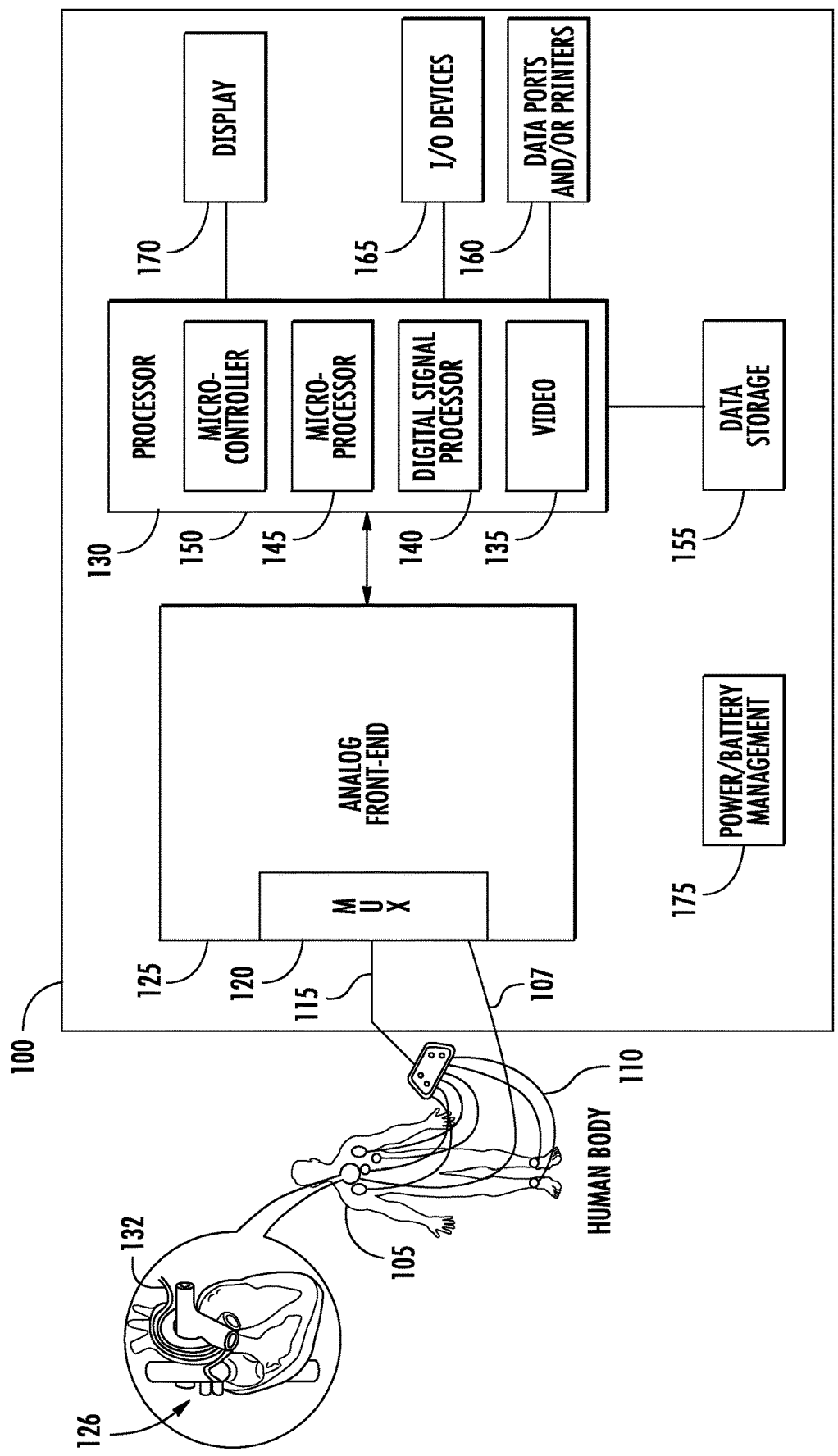
FIG. 1 is a block diagram of a device initializing catheter stability and speed to estimate impedance drop.

The present invention is related to electrocardiography, referred to herein as ECG, and may also be referred to as EKG. More particularly, the present invention is related to systems and methods for including catheter stability while estimating impedance drop during measurements and procedures.

Cardiac electrophysiology is the science of elucidating, diagnosing, and treating the electrical activities of the heart. One medical system that is used in this area is the CARTO system. In certain procedures, cardiac electrophysiology may be used to treat arrhythmias by ablating tissue surrounding the heart that is either the source of unwanted beats or conducts unwanted signals. After treatment, the ablation results in a denaturing of the tissue preventing the tissue from conducting the unwanted signals or beats. One of the physical characteristics of the ablation is that the electrical impedance between the ablating electrode contacting the tissue and the grounding patches on the body of the patient drops. During the procedure, this impedance is monitored to provide an indication of the effectiveness of the ablation procedure. The impedance provides an indication of when the ablation procedure is complete. Therefore, the measurement of impedance is an important and integral part of the ablation procedure and improvements in the ability to accurately measure the impedance are paramount.

The present machine for impedance drop estimation may be based on a weighted combination of a least squares filter and a median filter. The relative weight in combining the output of the two filters may be based on the catheter speed. In some implementations, the weighting between the output of two filters may be based on a logical sigmoid filter, and such filter may set the 50% threshold to 1 mm/sec of catheter speed. The use of the two filters combined using the weighting provides improved accuracy in compensating for the periodic impedance changes due to respiration and heartbeat as well as spikes in impedance that may result at the beginning of an ablation procedure. As will be understood in the present description, other weightings and filters may also be used.

A machine for measuring the impedance during a medical procedure being performed on a patient is disclosed. The machine include an electrode capable of being used in the medical procedure, a plurality of patches operationally located on the body surface of the patient, and a sensor for measuring a signal between the electrode and at least one of the plurality of patches, the signal being processed using a processor applying a first filter and a second filter separately, and combining the result of the output of the first filter and the output of the second filter using a weighting to provide an output of the impedance, wherein the impedance indicates an end of the medical procedure.

The machine may include the first filter biased to provide a more accurate assessment of the impedance during the course of the medical procedure is underway. The machine may include the first filter as a least squares filter.

The machine may include the second filter biased to provide a more accurate assessment of the impedance at the beginning of the medical procedure. The machine may include the second filter as a median filter. The machine may include the weighting as a sigmoid filter applied to the first and second filters based on catheter speed.

Electrocardiography, referred to herein as ECG, and may also be referred to as EKG, is the process of recording the electrical activity of the heart over a period of time using electrodes placed on the skin, or inside the heart using a specialized catheter (i.e. intracardiac ECG). These electrodes detect the small electrical changes that arise from the cardiac muscle's electro-physiologic pattern of depolarizing during each heartbeat. ECGs are commonly or routinely performed cardiology tests. The machine used in the test is an electrocardiograph and the initial output is an electrocardiogram. For the sake of brevity, electrocardiography, electrocardiograph, and electrocardiogram are all referred to herein as ECG, and may also be referred to as EKG.

An intracardiac electrogram (ICEG) is an ECG with some added intracardiac leads (i.e., inside the heart). Such an ICEG may be utilized in combination with, or in the alternative to, a conventional 12-lead ECG. In a conventional 12-lead ECG, 10 electrodes are placed on the patient's limbs and on the surface of the chest. The overall magnitude of the electrical potential of the heart is then measured from 12 different angles ("leads") and is recorded over a period of time. The procedure duration may vary from tens of minutes to several hours. During each procedure, there are usually several dozens of ablation sessions, each of which may last several seconds up to approximately 1 minute, for example. By way of example, a conventional 12-lead ECG may be performed over a period of time, such as 10 seconds, for example. In this way, the overall magnitude and direction of the electrical depolarization of the heart is captured at each moment throughout the cardiac cycle. A graph of voltage versus time produced by this medical procedure is referred to as an electrocardiogram.

During each heartbeat, a healthy heart has an orderly progression of depolarization. This orderly pattern of depolarization gives rise to the characteristic ECG tracing. To the trained clinician, an ECG conveys a large amount of information about the structure of the heart and the function of its electrical conduction system. Among other things, an ECG can be used to measure the rate and rhythm of heartbeats, the size and position of the heart chambers, the presence of any damage to the muscle cells or conduction system of the heart, the effects of cardiac drugs, and the function of implanted pacemakers. Interpretation of the ECG is fundamentally about understanding the electrical conduction system of the heart. Normal conduction starts and propagates in a predictable pattern, and deviation from this pattern can be a normal variation or be pathological.

As set forth above, cardiac electrophysiology is the science of diagnosing, and treating the electrical activities of the heart using, among other techniques, the ECG. The term is usually used to describe studies of such phenomena by invasive (intracardiac) catheter recording of spontaneous activity as well as of cardiac responses to programmed electrical stimulation (PES). These studies are performed to assess complex arrhythmias, elucidate symptoms, evaluate abnormal electrocardiograms, assess risk of developing arrhythmias in the future, and design treatment. Therapeutic methods include ablations. Ablation generally refers to the removal, killing or scarring of biological tissue, such as to alter the contraction patterns, usually by surgery, and may include methods of ablating aberrant tissue from within the body via minimally invasive procedures. In cardiac electrophysiology procedures, the dysfunctional tissue may be ablated using heat generated from alternating electric current at radio frequencies in the range of 350-500 kHz. As part of the ablation procedure, the ablation electrode, used in ablating the tissue, may be monitored for impedance as compared to patches on the body of the patient to determine how the procedure is progressing and when the procedure is complete. However, in order to monitor the impedance drop indicating when the procedure is complete other effects on the impedance measurement may need to be accounted for. These other effects include respiration of the patient, catheter stability, temperature, catheter force, catheter positional stability, and system noise.

FIG. 1 illustrates a block diagram of a device 100 utilizing catheter stability and speed to estimate impedance drop. Device 100 may take the form of an ECG. Device 100 includes a series of leads 110 that taper into a single multiplexed input 115. The series of leads 110 may be placed on a human test subject 105. Additional leads 107, which may be included with series of leads 110, or separate therefrom (as shown) may be intracardiac leads 107.

Intracardiac leads 107 may be used for diagnostic or therapeutic treatment, such as for mapping electrical potentials in a heart 126 of a patient 105. Alternatively, intracardiac leads 107 may be used, mutatis mutandis, for other therapeutic and/or diagnostic purposes in the heart or in other body organs.

Intracardiac leads 107 may be inserted in the vascular system of the patient 105 so that a distal end 132 of the leads 107 enters a chamber of the patient's heart 126. Although FIG. 1 shows a single lead 107 with a single location sensor, embodiments of the present invention may utilize probes with more than one location sensor.

The signals on the series of leads 110 are input into an analog front-end 125 via an input multiplexor 120. The analog front-end 125 provides to and is controlled by a processor 130. Processor 130 may include, as shown, a video controller 135, digital signal processor 140, a microprocessor 145, and a micro controller 150. Processor 130 is coupled to a data storage 155. Data ports and printers 160 may be coupled to processor 130. Other input/output devices 165 may be coupled to processor 130. A display 170 may be used to provide output of the signals of the ECG. A power/battery management system 175 may be included to provide power for device 100 to operate.

Series of leads 110 includes both the generally used forms of electrodes and leads. One or more of the series of leads 110 may include an ablation electrode. The series of leads 110 may include a conductive pad in contact with the body 105 that makes an electrical circuit with the electrocardiograph. On a standard 12-lead ECG there are only 10 leads 110. Series of leads 110 may be grouped into three sets: limb, augmented limb, and precordial. Generally, the 12-lead ECG has a total of three limb leads and three augmented limb leads arranged like spokes of a wheel in the coronal plane (vertical) and six precordial leads that lie on the perpendicular transverse plane (horizontal).

Analog front-end 125 receives the signals from the series of leads 110 and performs analog processing, such as filtering, of the signals.

Data storage 155 is any device that records information. Data storage may provide a storage medium for the signals includes within device 100 and a place for calculations of processor 130 to be stored.

Microprocessor 145 may be a computer processor which incorporates the functions of a computer's central processing unit (CPU) on a single integrated circuit (IC), or a few integrated circuits. Microprocessor 145 may be a multipurpose, clock driven, register based, programmable electronic device which accepts digital or binary data as input, processes it according to instructions stored in its memory or data storage 155, and provides results as output. Microprocessor 145 contains both combinational logic and sequential digital logic.

Micro controller 150 may be one or more small computers on a single integrated circuit. Micro controller 160 may contain one or more CPUs along with memory and programmable input/output peripherals. Program memory in the form of Ferroelectric RAM, NOR flash or OTP ROM is also often included on chip, as well as a small amount of RAM. Microcontrollers are designed for embedded applications, in contrast to the microprocessors used in personal computers or other general purpose applications consisting of various discrete chips.

Digital signal processor (DSP) 140 may perform digital signal processing to perform a wide variety of signal processing operations. The signals processed in this manner are a sequence of numbers that represent samples of a continuous variable in a domain such as time, space, or frequency. Digital signal processing can involve linear or nonlinear operations. Nonlinear signal processing is closely related to nonlinear system identification and can be implemented in the time, frequency, and spatio-temporal domains. The application of digital computation to signal processing allows for many advantages over analog processing in many applications, such as error detection and correction in transmission as well as data compression. DSP is applicable to both streaming data and static (stored) data.

The system of FIG. 1 may calculate or measure the impedance drop during an ablation procedure. The calculated impedance may serve as an input in determining whether the ablation is complete. The system for impedance drop estimation is based on a weighted choice between a least squares filter and a median filter. The relative weight when combining the results from each of the two filters is based on the catheter speed. In one embodiment, the weighting is based on a logical sigmoid filter with the 50% threshold set to 1 mm/sec of the catheter speed. This weighting may provide a more accurate way to compensate for apparent periodic impedance changes due to respiration and heartbeat. Other weightings and filters could also be used.

A system and method for measuring the impedance during a medical procedure on a patient is disclosed. The system and method include an electrode 110 capable of being used in the medical procedure, a plurality of patches (not shown in FIG. 1) operationally located on the body surface of the patient, and a sensor for measuring a signal between the electrode 110 and at least one of the plurality of patches, the signal being processed using processor 130 applying a first filter and a second filter, and combining the result of the first filter and the second filter using a weighting of the filters to provide a measurement of the impedance, wherein the impedance indicates the end of the medical procedure.

A first fitting method or filter may be used for combining with a second method or filter. The first filter may be designed to provide a more accurate assessment of the impedance once the test is underway. The first filter may use a least square filter. Generally, a least square filter minimizes the sum of squared residuals with a residual being the difference between an observed value, and the fitted value provided by a model.

A minimum filter length may be set. According to an embodiment, the minimum filter length is 5 seconds. For a given time interval, where each impedance sample has a timestamp, the algorithm provides a linear equation in the form Y=aX+b, where X represents the timestamp and Y represents the predicted filtered impedance value. Variable b is the mean of the impedance values in a given time span. Variable mid represents the position index associated with b and $$mid = \text{Ceiling}\left(\frac{\text{number of positions}}{2}\right).$$

The ceiling of a number is the nearest integer above a number. Variable $t_{mid}$ represents the timestamp associated with the index mid and $\Delta t_i = t_i - t_{mid}$, for a given sample i. Then $\Delta y_i = y_i - b$, for a given sample i. If "a" is defined according to Equation 1:

$$a = \sum_{i=-n}^{n} \Delta t_i \cdot \Delta y_i / \sum_{i=-n}^{n} \Delta t_i^2 \qquad \text{Equation 1.}$$

Given any impedance value having the timestamp $t_p$, its predicted impedance value $y_p$ may be determined according to Equation 2:

$$y_p = a \cdot \Delta t_p + b, \text{ where } \Delta t_p = t_p - t_{mid} \qquad \text{Equation 2.}$$

This method is complicated by the first five seconds of an ablation. For the first five seconds, the interval window does not travel. The result is that the filtered impedance is simple linear with time, the line drawn between the first sample and the sample at 5 seconds. That is, each point is only the underlying data point as there are no enough other data points to consider in the window.

A second fitting method or filter may be used to overcome this complication. The second filter may be designed to provide a more accurate assessment of the impedance at the beginning of the test. The second filter may use a median filter.

Generally, the median filter provides a non-linear technique that may be used to remove noise. The median filter may be applied to pre-process the data such that the results of ablation are improved. The main idea of the median filter is to run through the signal data point by data point, replacing each data point with the median of neighboring data points. The number of neighboring data points used in the calculation for a given median is determined by the window. This window may be defined to be several data points wide, i.e., 200, and may last seconds, i.e., 10, for example.

The present system may also provide a method for indicating when each of the two filters is used. This is described herein as a weighting of the filters. For example, the system may use one filter until a certain time period during the test, such as 5 seconds, for example, and then switch to the other filter. Alternatively, the first filter may be used until a certain time from the test initiation, at which time the outputs of the two filters are averaged until a later time, then at the later time, the second filter is used alone. Generally, the weighting the filters may provide a methodology for using the outputs of each filter to provide a single output. The first filter may be used for a period of time, and then phased out over a period of time while a second filter is phased in. The weighting of the filters may utilize a sigmoid filter to combine the outputs of each of the filters into a single output.

A sigmoid filter may be provided by a mathematical function having an "S" shaped curve (sigmoid curve). The sigmoid filter refers to the function defined by the formula $$y = \frac{1}{1 + e^{-x}}.$$

The sigmoid filter may provide a methodology to combine the results of the first and second filters while enabling the impedance result to more heavily favor the second filter at the beginning of the medical procedure and then favor the first filter once the medical procedure is underway.

Figure 2:
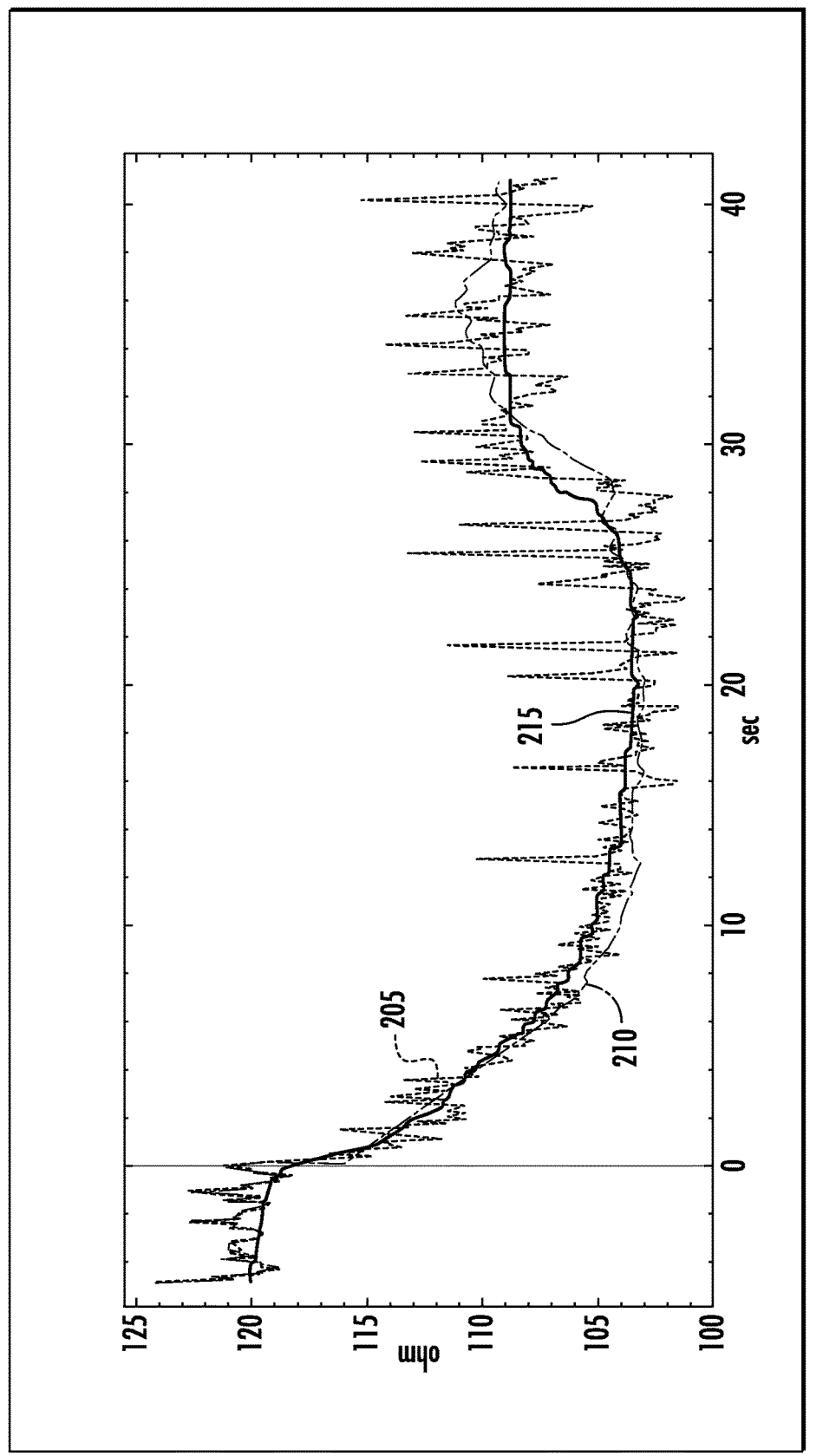
FIG. 2 illustrates a graph of the impedance in ohms versus time in seconds for a generally well-behaved ablation procedure.

During many medical procedures, the impedance drop may be a relatively smooth curve as shown in FIG. 2. FIG. 2 illustrates a graph 200 of the impedance in ohms versus time in seconds for a generally well-behaved ablation procedure. Line 205 represents the measured impedance, line 210 is the least squares fit of the impedance drop, and line 215 is fit of the impedance drop using a median filter.

Line 215 is a fit based on a median filter in order to determine the impedance drop. As may be seen in FIG. 2, line 215 displays fairly accurate tracking of the impedance from times before 0 seconds throughout the time frame of the plot.

Line 205 illustrates the measured impedance. The oscillations in line 205 generally are attributable to the respiratory and cardiac cycles of the patient. These are artifacts largely due to changes in the contact of the catheter with the tissue. That is, the impedance does not readily include these jumps.

Line 210 is the fit using a least square filter to determine the impedance drop. This fit for line 210 is based on least squares fitting that is characterized by a linear descent in the first five seconds. Use of a median filter with the data is shown as line 215. Both methods, shown by line 210 and line 215, track the data fairly well which is expected for well-behaved functions.

Figure 3:
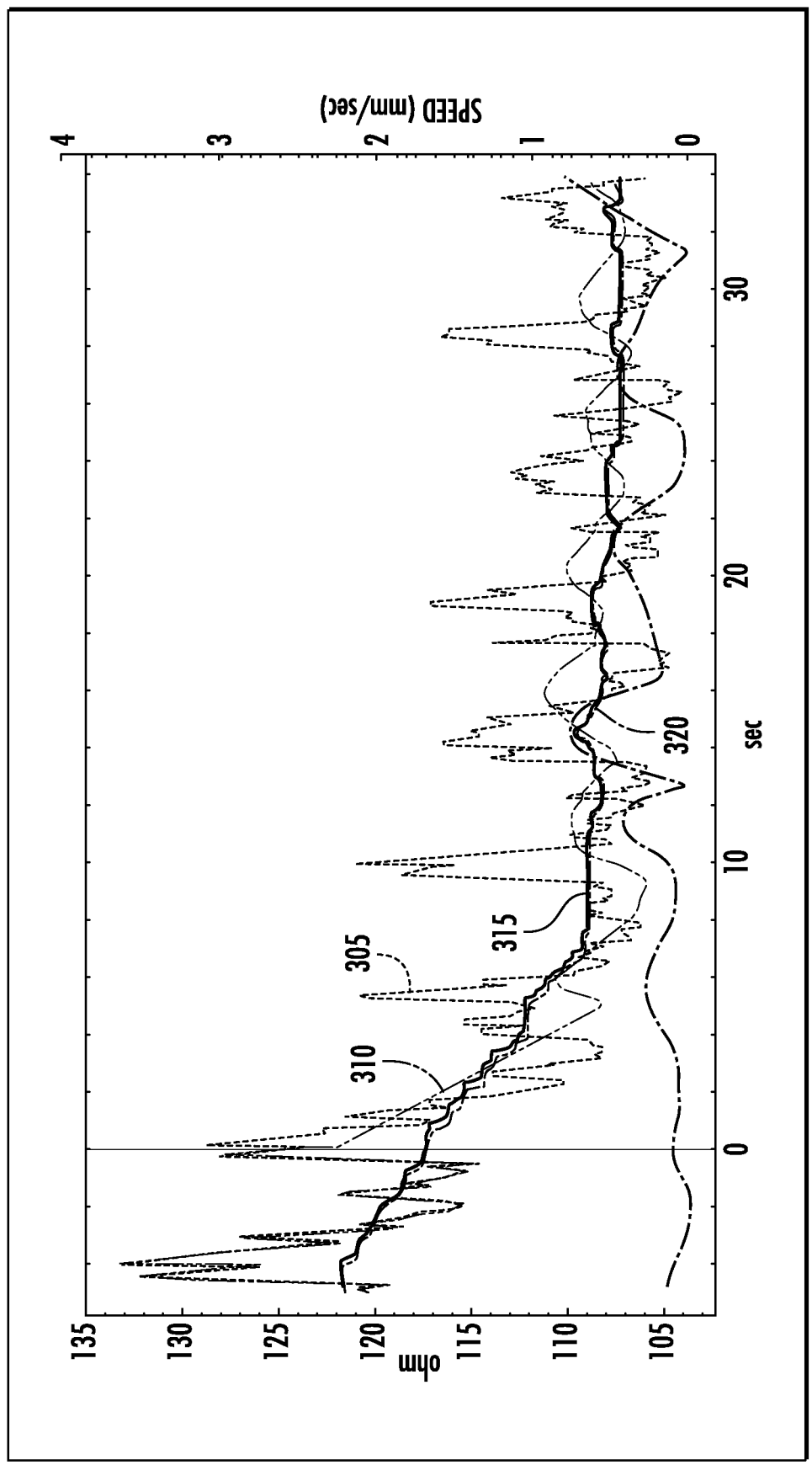
FIG. 3 illustrates a graph of the impedance in ohms versus time in seconds indicating correlated respiration fluctuations.

FIG. 3 illustrates a graph 300 of the impedance in ohms versus time in seconds for an overestimation of impedance drop because of correlated respiration fluctuations. Line 305 represents the measured impedance, line 310 is the linear fit of the impedance drop using a least squares filter, and line 315 is a fit of the impedance drop using a median filter. Line 320 depicts the catheter speed in mm/sec plotted as a function of time in seconds. In graph 300, the time begins before the ablation procedure commences at time t=0 seconds.

Line 305 illustrates the measured impedance. The oscillations in line 305 are attributable to the respiratory cycle of the patient. As set forth above, the oscillations are artifacts that are due to tissue catheter pressure changes.

Line 310 is a fit used to determine the impedance drop using the least squares filter. This fit for line 310 is based on least squares fitting that is characterized by a linear descent in the first five seconds. The start of the ablation corresponds to a peak in impedance artifact correlated with the respiratory cycle. As a result, the initial impedance and, therefore, the resulting impedance drop are overestimated.

Line 315 is a fit based on a median filter in order to determine the impedance drop. As may be seen in FIG. 3, line 315 displays a better estimate of the impedance by comparing to line 305 as the measured impedance than does any other fit depicted in FIG. 3.

In order to account for the catheter positional stability, the respiratory compensated catheter speed illustrated as line 320 is considered. Inspection of line 320 shows that the catheter speed is below 0.5 mm/sec for most of the session, especially during the first 10 seconds, indicating a stable catheter. For a stable catheter, the median filter may provide the best path. As is illustrated in FIG. 3, line 315 represents a better estimate of the impedance as compared to the least squares fit line 310. This may be demonstrated by doing a quality of fit check, such as by using a sum of squares of point by point differences between measurements and each filter, or by examining trends over the graph.

Figure 4:
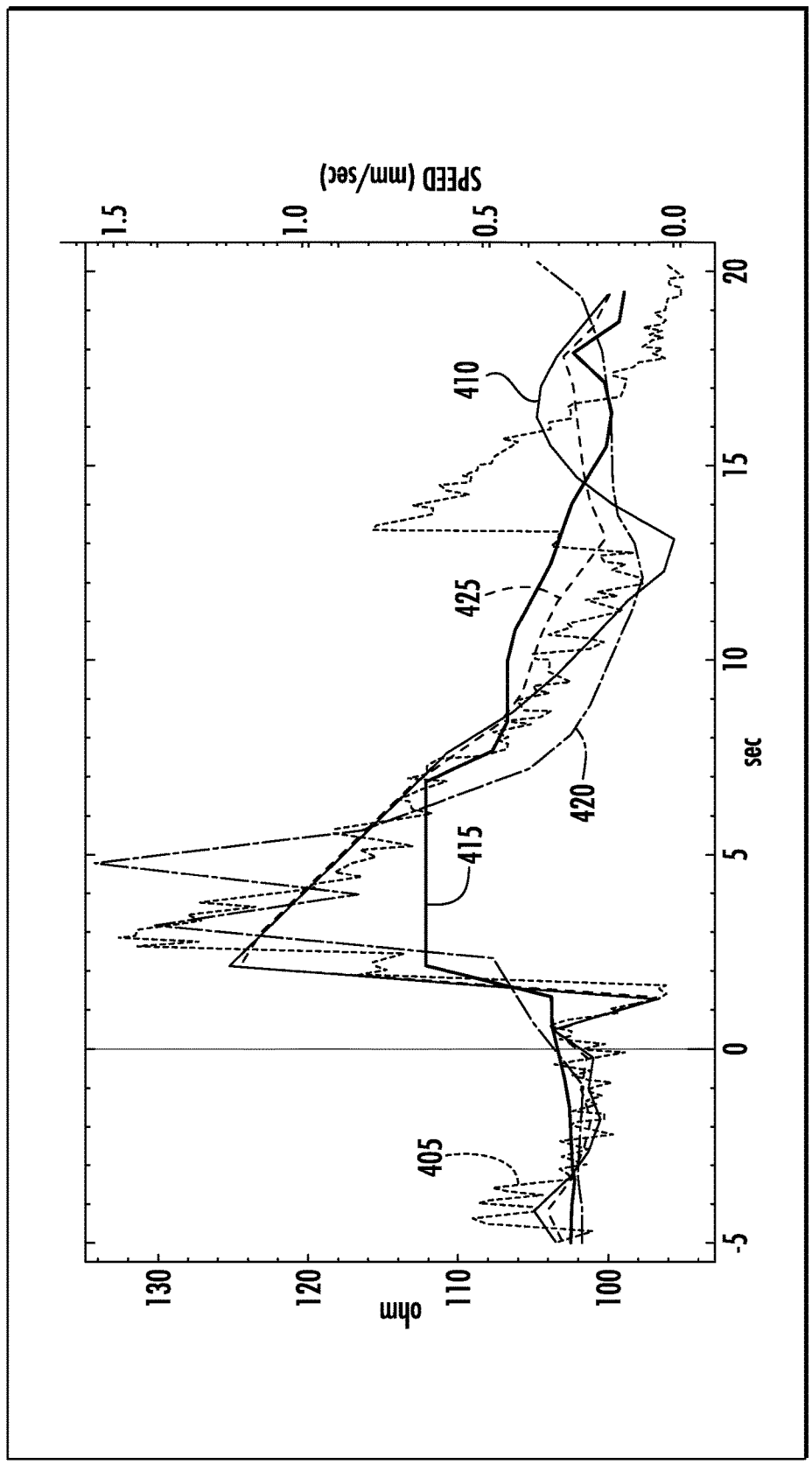
FIG. 4 illustrates a graph of the impedance in ohms versus time in seconds that illustrates the large jump in impedance at the start of the ablation procedure.

FIG. 4 illustrates a graph 400 of the impedance in ohms versus time in seconds that illustrates the large jump in impedance at the start of the ablation procedure. Line 405 represents the measured impedance, line 410 is the least squares filter of the impedance drop, and line 415 is the median filter of the impedance drop. Line 420 depicts the respiratory compensated catheter speed in mm/sec plotted as a function of time in seconds. A sudden change in the catheter speed is an indication of catheter instability. Line 425 depicts a combination of the median filter and the least squares filter of the impedance drop. The median filter and the least squares filter may be combined using a weighting of the filters as described. For the line 425 of FIG. 4, the weighting uses the described sigmoid filter. In graph 400, the time begins before the ablation procedure commences at time t=0 seconds.

As seen by comparing line 405 and line 420, the impedance jump is correlated with sudden catheter motion. The linear filter method shown in line 410, which fixes on the maximum point at the beginning of the ablation, matches the measured value better than the median filter, as the median filter is influenced by the low values before the ablation start. The weighted combination of the two methods shown in 425 successfully interpolates between the two filtering methods. In this case the weighted factor is a sigmoid filter, described below with respect to FIGS. 5 and 6, utilized to combine the two filtered results. As is illustrated in graph 400, the combined line 425 provides a better fit to the impedance than either the median or least squared filter alone. This may be illustrated with quality of fit as defined above using the sum of the squares of the residuals.

Figure 5:
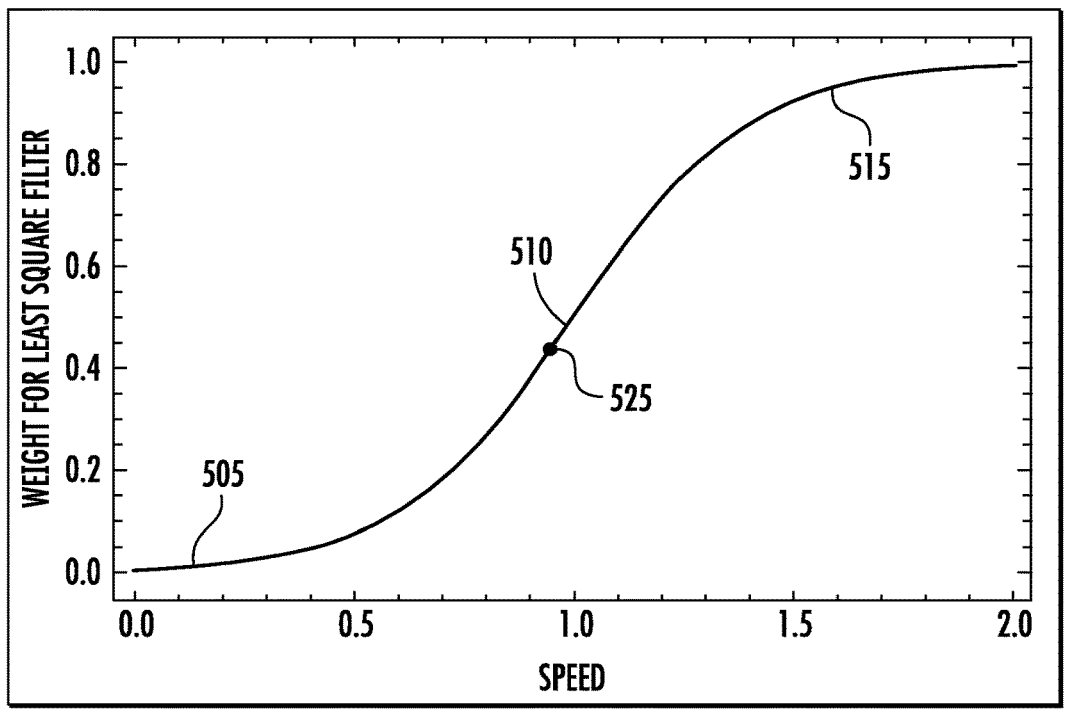
FIG. 5 illustrates a sigmoid filter to apply as the weight applied to the result of the least square filter illustrated in a plot of the weight for the least square filter against the speed of the catheter.

FIG. 5 illustrates a sigmoid filter to apply as the weighted factor applied to the result of the least square filter illustrated in a plot 500 of the weight for the least square filter against the speed of the catheter. The applied weight for the least square filter as a function of catheter speed is shown by curve 510. Curve 510 illustrates a sigmoid filter that starts with the applied weight for the least square filter small as compared to the catheter speed such as portion of the graph 505. As the speed approaches 1.0 mm/sec, the applied weight for the least square filter is 0.5 at point 525. Point 525 and curve 510 may be set based on any number of characteristics. As shown the half point on curve 510 at 0.5 is set to a catheter speed of 1 mm/sec. A speed of 1.0 mm/sec may represent a nominal or average speed used during the procedure. Curve 510 illustrates a sigmoid filter that ends with the applied weight for the least square filter large as compared to the higher catheter speeds such as portion of the graph 515.

Figure 6:
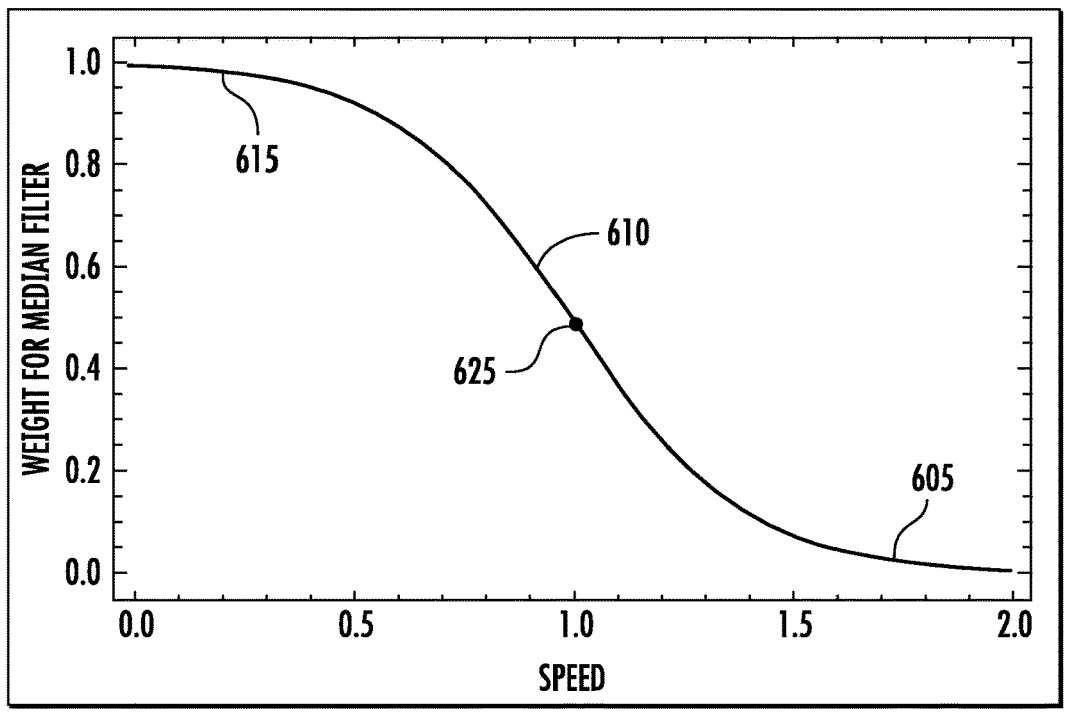
FIG. 6 illustrates a sigmoid filter to apply as the weight applied to the result of the median filter illustrated in a plot of the weight for the median filter against the speed of the catheter.

FIG. 6 illustrates a sigmoid filter to apply as the weighted factor applied to the result of the median filter illustrated in a plot 600 of the weight for the median filter against the speed of the catheter. The applied weight for the median filter as a function of catheter speed is shown by curve 610. Curve 610 illustrates a sigmoid filter that starts with the applied weight for the median filter large as compared to the catheter speed such as portion of the graph 615. As the speed approaches 1.0 mm/sec, the applied weight for the median filter is 0.5 at point 625. Point 625 and curve 610 may be set based on any number of characteristics. As shown the half point on curve 610 at 0.5 is set to a catheter speed of 1 mm/sec. A speed of 1.0 mm/sec may represent a nominal or average speed used during the procedure. Curve 610 illustrates a sigmoid filter that ends with the applied weight for the median filter small as compared to the higher catheter speeds such as portion of the graph 605.

Figure 7:
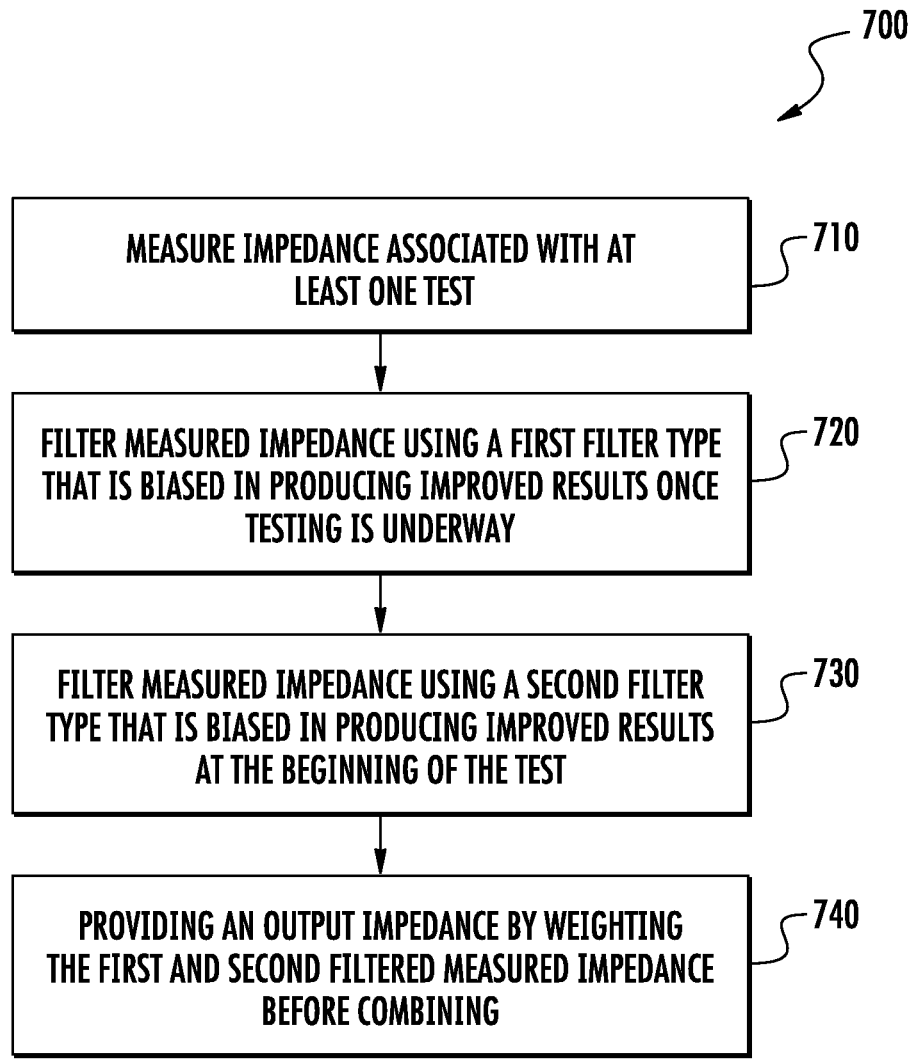
FIG. 7 illustrates a method of measuring the impedance during a medical procedure being performed on a patient.

FIG. 7 illustrates a method 700 of measuring the impedance during a medical procedure being performed on a patient. Method 700 includes measuring the impedance associated with the at least one test or medical procedure at step 710. At step 720, method 700 includes filtering the measured impedance using a first filter that is generally biased in providing improved results once testing or the medical procedure is underway. At step 730, method 700 includes filtering the measured impedance using a second filter that is generally biased in providing improved results at the beginning of the test or medical procedure. At step 740, an output impedance is provided by weighting the first and second filtered measured impedance results and combining.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A device for measuring impedance during a medical procedure being performed on a patient, the device comprising:
    an electrode capable of being used in the medical procedure;
    a plurality of patches operationally located on a body surface of the patient; and
    a sensor for measuring a signal between the electrode and at least one of the plurality of patches,
    the signal being processed using a processor using a first filter and a second filter, and combining the result of the first filter and the second filter using a weighting of the result of the first and second filters to provide a measurement of the impedance, the weighting including a first weight associated with the first filter result and a second weight associated with the second filter result, wherein during a first period of the measurement the first weight is greater than the second weight and during a second period of the measurement the second weight is greater than the first weight, and wherein the measured impedance indicates the end of the medical procedure.

2. The device of claim 1 wherein the first filter is a least squares filter.

3. The device of claim 1 wherein the second filter is a median filter.

4. The device of claim 1 wherein the weighting of filters includes a sigmoid filter.

5. The device of claim 1 wherein the weighting of the filters accounts for the temperature of the electrode.

6. The device of claim 1 wherein the weighting of the filters is based on the speed of the electrode.

7. The device of claim 1 wherein the first filter improves the assessment of the impedance once the medical procedure is underway.

8. The device of claim 1 wherein the second filter improves the assessment of the impedance at the beginning of the medical procedure.

9. The device of claim 1 wherein the electrode is included as part of a catheter.

10. The device of claim 1 wherein the medical procedure is an ablation.

11. A method for measuring impedance using a device during a medical procedure being performed on a patient, the method comprising:
    measuring the impedance associated with the medical procedure using a sensor capable of measuring a signal between an electrode and at least one of a plurality of patches;
    filtering the measured impedance using a first filter to produce a first impedance result;
    filtering the measured impedance using a second filter to produce a second impedance result; and
    providing an output impedance by combining the first impedance result with the second impedance result using a weighting of the first impedance result and the second impedance result, the weighting including a first weight associated with the first impedance result and a second weight associated with the second impedance result, wherein during a first period of the measurement the first weight is greater than the second weight and during a second period of the measurement the second weight is greater than the first weight.

12. The method of claim 11 wherein the first filter is a least squares filter.

13. The method of claim 11 wherein the first filter improves the assessment of the impedance once the medical procedure is underway.

14. The method of claim 11 wherein the second filter is a median filter.

15. The method of claim 11 wherein the second filter improves the assessment of the impedance at the beginning of the medical procedure.

16. The method of claim 11 wherein the combining occurs using a weighting of first and second impedance results.

17. The method of claim 16 wherein the weighting comprises a sigmoid filter.

18. The method of claim 17 wherein the weighting accounts for the temperature of an electrode used in the medical procedure.

19. The method of claim 17 wherein the weighting is based on the speed of an electrode used in the medical procedure.

20. The method of claim 11 wherein the electrode is included as part of a catheter and the medical procedure is an ablation.

* * * * *

UNITED STATES PATENT AND TRADEMARK OFFICE
CERTIFICATE OF CORRECTION

PATENT NO. : 10,610,296 B2
APPLICATION NO. : 15/610253
DATED : April 7, 2020
INVENTOR(S) : Avram Dan Montag et al.

It is certified that error appears in the above-identified patent and that said Letters Patent is hereby corrected as shown below:

In the Specification

In Column 4, Line 15, delete "human test subject 105." and insert -- patient 105. --, therefor.
In Column 4, Lines 45-46, delete "body 105" and insert -- patient 105 --, therefor.
In Column 5, Line 5, delete "Micro controller 160" and insert -- Micro controller 150 --, therefor.
In Column 6, Line 52, delete "weighting the" and insert -- weighting of the --, therefor.
In Column 9, Lines 15-16, delete "and combining." and insert -- before combining. --, therefor.

Signed and Sealed this
Nineteenth Day of March, 2024

Katherine Kelly Vidal
*Director of the United States Patent and Trademark Office*